United States Patent [19]

Christensen et al.

[11] 4,255,330
[45] Mar. 10, 1981

[54] PROCESS FOR PREPARING 6-SUBSTITUTED AMINO-2-SUBSTITUTED-PEN-2-EM-3-CARBOXYLIC ACID

[75] Inventors: Burton G. Christensen, Metuchen; Frank P. DiNinno, Old Bridge, both of N.J.

[73] Assignee: Merck & Co., Inc., Rahway, N.J.

[21] Appl. No.: 108,605

[22] Filed: Dec. 31, 1979

Related U.S. Application Data

[60] Division of Ser. No. 948,712, Oct. 10, 1978, abandoned, which is a continuation-in-part of Ser. No. 852,274, Nov. 17, 1977, abandoned.

[51] Int. Cl.³ ............................................. C07D 499/04
[52] U.S. Cl. .......................... 260/239.1; 260/245.2 R
[58] Field of Search ...................... 260/239.1, 245.2 R

[56] References Cited

U.S. PATENT DOCUMENTS

| | | | |
|---|---|---|---|
| 4,058,521 | 11/1977 | Uyeo et al. | 260/239.1 |
| 4,164,497 | 8/1979 | Kamiya et al. | 260/239.1 |

*Primary Examiner*—Natalie Trousof
*Assistant Examiner*—Vera C. Clarke

*Attorney, Agent, or Firm*—James A. Arno; Julian S. Levitt

[57] ABSTRACT

Disclosed are 6-substituted amino-2-substituted-pen-2-em-3-carboxylic acids of the following structure:

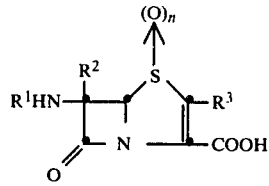

wherein
$R^1$ is hydrogen or acyl, $R^2$ is hydrogen or methoxyl, and $R^3$ is, inter alia, hydrogen, —R, —OR, —SR, —NR$_2$; R is alkyl, aryl, aralkyl, heterocyclyl or heterocyclylalkyl; n is 0 or 1; when n=1, $R^3$ is not —SR. Such compounds and their pharmaceutically acceptable salt, and ester derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

PROCESS FOR PREPARING 6-SUBSTITUTED AMINO-2-SUBSTITUTED-PEN-2-EM-3-CARBOXYLIC ACID

This is a division of application Ser. No. 948,712 filed Oct. 10, 1978, which in turn is a continuation-in-part of U.S. patent application Ser. No. 852,274 filed Nov. 17, 1977, both now abandoned.

BACKGROUND OF THE INVENTION

This invention relates to 6-substituted amino-2-substituted-pen-2-em-3-carboxylic acids and their pharmaceutically acceptable salts and esters, which compounds are useful as antibiotics and which may be represented by the following generic structural formula (I):

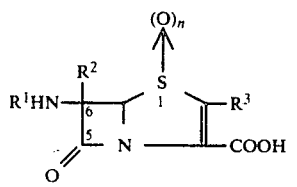

wherein $R^1$ is hydrogen or acyl, $R^2$ is hydrogen or methoxyl and $R^3$ is inter alia, hydrogen, —R, —OR, —SR, —NR$_2$; R is alkyl, aryl, aralkyl, heterocyclyl or heterocyclylalkyl; n=0 or 1; when n=1, $R^3$ is not —SR.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as S. aureus, Strep. pyogenes, and B. subtilis, and gram negative bacteria such as E. coli, Pseudomonas, Proteus morganii, Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

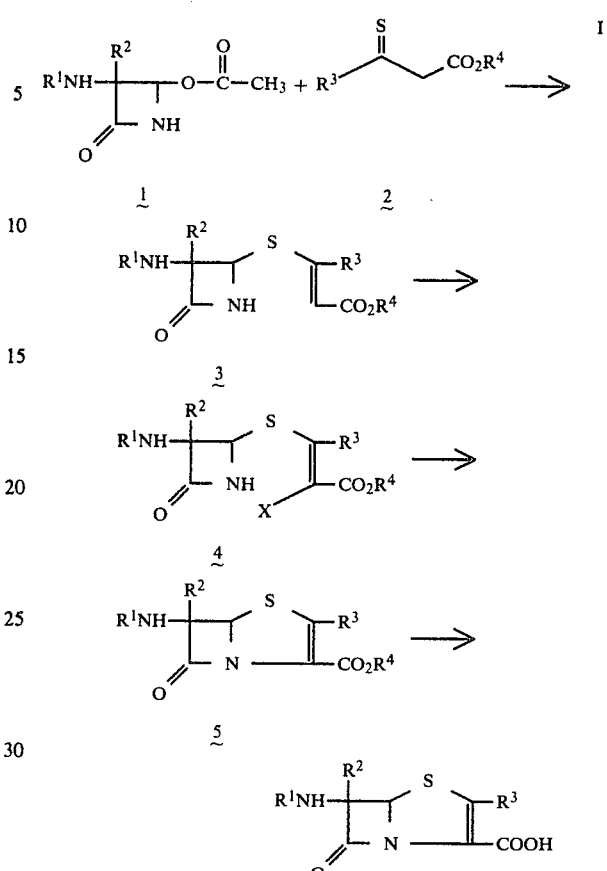

In words relative to the above diagram, the starting azetidinone 1 is treated with a 3-thionopropionic acid ester derivative (2) in the presence of a base such as NaOCH$_3$, Al[OCH(CH$_3$)$_2$]$_3$, (CH$_3$CH$_2$)$_3$N and the like in a solvent such as methanol, tetrahydrofuran (THF), CH$_2$Cl$_2$ and the like at a temperature of from 0° to 22° C. for from 1 hour to overnight to provide the seco-lactam (3). Relative to these reactions, $R^4$ is a readily removable carboxyl blocking group such as p-nitrobenzyl, t-butyl, trichloroethyl or the like; and $R^1$, $R^2$ and $R^3$ are as defined above. Halogenation of 3 yields 4 wherein X is halo, such as chloro or bromo. Suitable halogenating agents include N-chlorosuccinimide, N-bromosuccinimide, N-bromoacetamide and the like; and the reaction 3→4 is conducted in the presence of the halogenating agent of choice in a solvent such as THF, benzene, benzene-ether and the like at a temperature of from −78° to 60° C. for from 0.5 to 2 hours. Cyclization of 4 to provide 5 is accomplished by treating 4 with a strong base such as lithiumdiisopropylamide, lithiumhexamethyldisilamide, lithiumtetramethylpiperidide or the like in a solvent such as tetrahydrofuran, hexamethylphosphoramide, dimethoxyethane or the like in the presence of a metal complex coupling agent at a temperature of from −78° to 22° C. for from 0.5 to 18 hours; suitable metals include Cu(I), the platinum metals such as Pd°; Ni°, Ni(II) and the like; representative complexes include cuprous iodide, cuprous bromide-dimethylsulfide complex, cuprous iodide-tri-n-butylphosphine complex, tetrakistriphenyl phosphine Pd(O), tetrakistriphenyl phosphine Ni(O), biscyclooctadienyl Ni(O), bis(diphenylphosphino)-ethane Ni(II).Cl$_2$ or the like. The fully protected intermediate 5 is deblocked to provide I. When the preferred blocking groups are employed, that is, $R^4$ is p-nitrobenzyl or trichloroethyl, the deblocking reaction may be accomplished by hydrogenation or zinc mediated reduction according to well-known procedures. A representative deblocking procedure comprises treating 5 in a solvent such as ethylacetate under hydrogen (1–40 atmospheres) at a temperature of 0° to 22° C. for from 0.25 to 2 hours in the presence of a hydrogenation catalyst such as 10%Pd/C, 5%Pd/BaCo₃, 5%Pt/C or the like.

The starting azetidinone material 1 may conveniently be prepared by the following scheme:

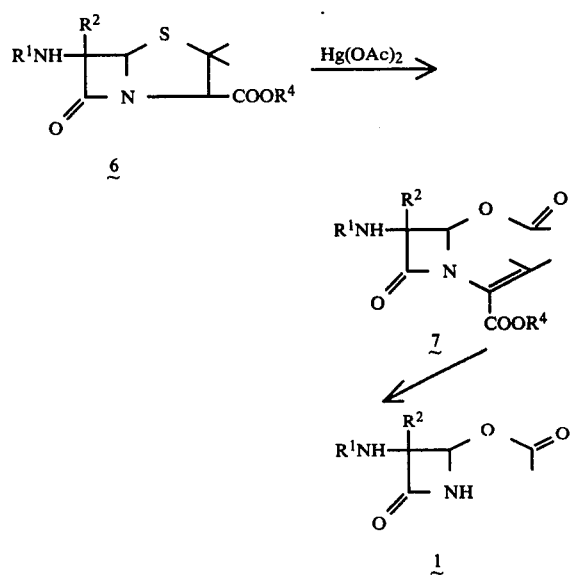

wherein $R^1$, $R^2$ and $R^4$ are as defined above.

In words relative to the above diagram, starting material 6 is cleaved with mercuric acetate in acetic acid solution at a temperature of from 22° C. to 110° C. for from 0.25 hours to 8 hours to provide the acetoxy lactam 7. Relative to these reactions, $R^4$ is a selected carboxyl protecting group such as methyl, benzyl, trichloroethyl or the like. Removal of the isopropylidene ester function is accomplished by treating 7 with potassium permanganate, osmium tetroxide or the like in a solvent such as aqueous pyridine, aqueous acetone or the like at a temperature of 0° to 22° C. for from 0.25 to 2 hours, to provide azetidinone 1. Analgous procedures are known in the literature; see, for example: E. G. Brain, et al., *J. Chem. Soc., Perkin I*, 447 (1976); R. J. Stoodley and N. R. Whitehouse, ibid., 32 (1973).

Starting material 2, in the above-described synthesis, may conveniently be prepared in a variety of ways reported in the literature. One preferred method, when the ultimate 2-substituent, $R^3$, (Structure I) is —SR, is shown in the following scheme:

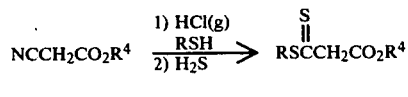

In words relative to the above diagram, the cyanoacetic acid ester 8 is treated with gaseous hydrogen chloride in a solvent such as benzene, diethylether, tetrahydrofuran or the like in the presence of a mercaptan (RSH) at a temperature of from 0° C. to 25° C. for from 0.25 to 1 hour. The resulting mixture is stirred at a temperature of from 0° C. to 80° C. for from 8 to 96 hours. The precipitate formed is collected by filtration and is dissolved in anhydrous dimethylsulfoxide or dimethylformamide or the like. The mixture is treated with gaseous hydrogen sulfide at a temperature of from 0° C. to 25° C. for from 10 min. to 24 hours and is stirred further at a temperature of from 0° C. to 25° C. for from 2 to 24 hours to provide 2. Relative to these reactions R and $R^4$ are as previously defined.

The following list representatively illustrates suitable starting materials 2. Such reagents are employed as described in the above procedure to provide species bearing a preferred —SR substituent at the 2-position.

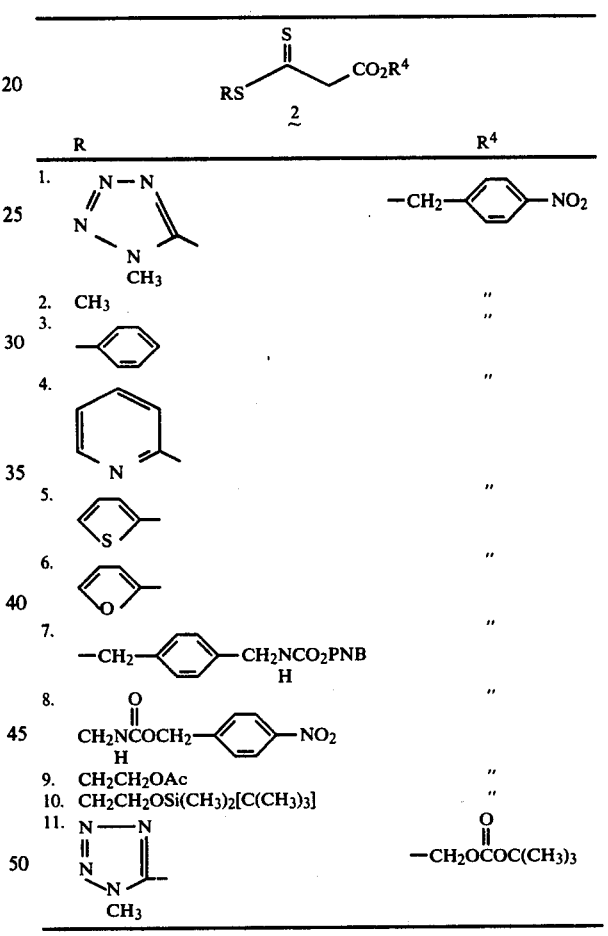

When starting material 2, in the above-described synthesis, provides the 2-substituent as —R, it may be prepared by known literature procedures: F. Duus, et al., *Ark. Kemi*, 29, 191 (1968); *Chem. Abs.*, 69:31404p (1968).

A schematic summary of such a convenient process is given below:

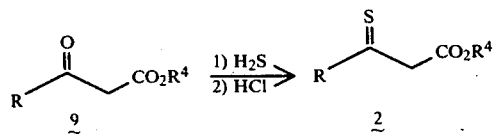

In words relative to the above diagram, the readily available substituted 3-ketoproprionic acid ester derivatives 9 is treated with hydrogen sulfide gas for from 1 to 3 hours in a solvent such as acetonitrile, dimethylformamide, dimethylsulfoxide or the like at a temperature of from −60° to 25° C. The mixture is then treated with gaseous hydrogen chloride for from 0.5 to 2 hours at a temperature of from −60° to 25° C. to provide starting material 2. Relative to this reaction, R and R⁴ are as previously described.

The following list representatively illustrates suitable starting materials 2. Such reagents are employed as described in the above procedure to provide species bearing a preferred —R substituent at the 2-position.

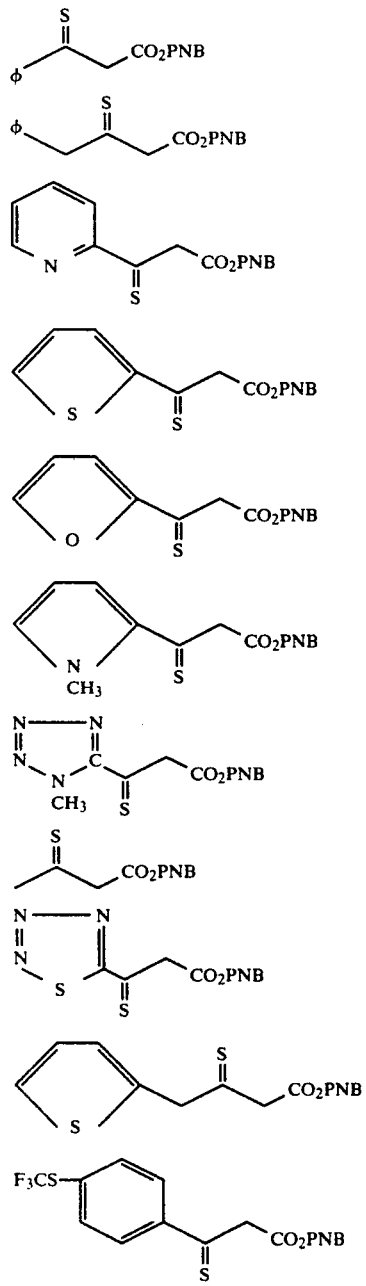

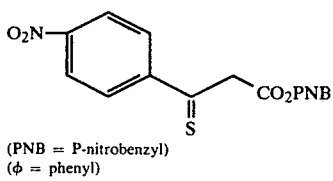

(PNB = P-nitrobenzyl)
(φ = phenyl)

An alternative procedure, which is especially suitable for embodiments wherein R³ is H or R, but not —OR, —SR, or —NR₂ is illustrated below:

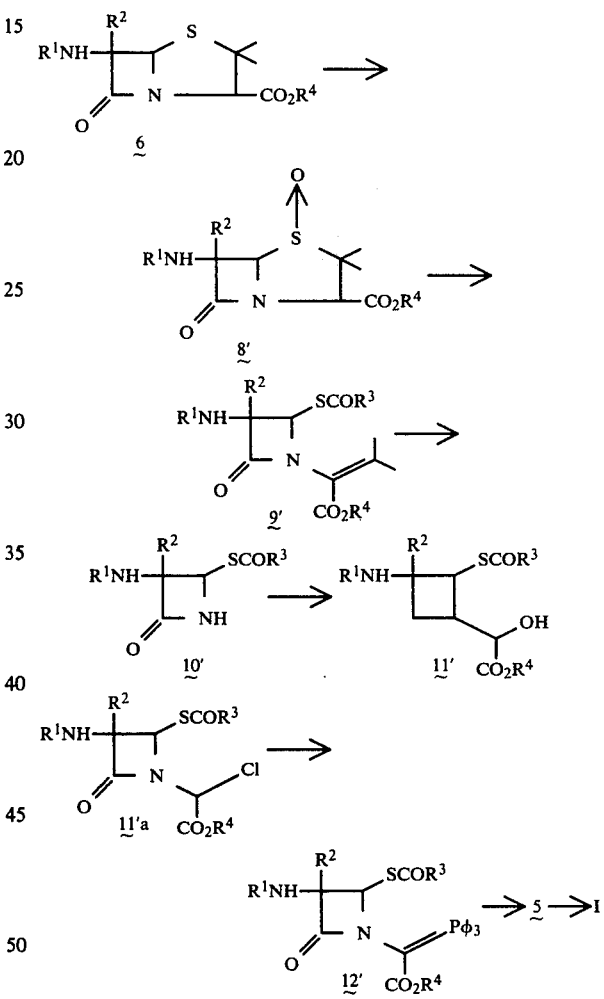

wherein all symbolism is as previously defined, R is aryl such as phenyl and substituted phenyl; φ is phenyl.

In word relative to the above reaction diagram, above-defined starting material 6 is taken through the scheme 6→12' whereupon 12' is converted to above-defined species 5 which is deblock as previously described to yield I. The oxidation reaction 6→8' is known and is conveniently accomplished by treating 6' in a solvent such as methylene chloride, chloroform, dioxane, tetrahydrofuran or the like at a temperature of from 0°–25° C. with a stoichiometric amount of an oxidizing agent such as m-chloroperbenzoic acid, perbenzoic and hydrogen peroxide, peracetic acid, or the like. The resulting sulfoxide 8', after isolation by conventional work-up, in a solvent such as benzene, toluene, dioxane, or the like is treated with a stoichiometric to slight excess of a phosphine such as tri-n-butylphosphine, trimethylphosphite, triphenylphosphite, or the like and a stoichiometric to ten-fold excess of the anhydride $(R^3CO)_2O$ (for example, substituted or unsubstituted benzoic anhydride). The mixture is typically heated under nitrogen for from 0.5 to 10 hours at a temperature of from 50° C. to reflux to yield $\underline{9}'$, which may be isolated by conventional work-up. In cases where the isomerization of the β,γ-unsaturated ester to the α,β-unsaturated ester does not occur under the reaction conditions or during work-up, the product is conveniently isomerized to the latter (as in $\underline{9}'$) with triethylamine. Cleavage of $\underline{9}'$ to provide $\underline{10}'$ is typically accomplished by treating $\underline{9}'$, in a solvent such as 8:1 acetone-water, aqueous pyridine, or the like with an equivalent to three-fold excess amount of an oxidizing agent such as potassium permanganate, osmium tetroxide, sodium periodate, or the like at a temperature of from 0° to 25° C. for from 5 min. to 1.0 hr., after which the reaction is quenched and $\underline{10}'$ isolated by conventional work-up. The reaction $\underline{10}' \rightarrow \underline{11}'$ is accomplished by treating $\underline{10}'$ with an excess of glyoxalate ester such as p-nitrobenzyl-glyoxalate hydrate. The reaction is conveniently carried out in a solvent such as benzene, toluene, xylene or the like at a temperature of from about 25° C. to reflux under a nitrogen atmosphere for from about 2 to 10 hours. The reaction $\underline{11}' \rightarrow \underline{11}'a \rightarrow \underline{12}'$ may be conducted stepwise. The halogenation reaction $\underline{11}' \rightarrow \underline{11}'a$ may be conducted by any of a variety of well-known halogenation means. Suitable reagents include: $SOCl_2$, $POCl_3$, oxalyl chloride and the like. A preferred means of chlorination involves treating $\underline{2}$ in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hr. The resulting species, $\underline{11}'a$, is isolated, if desired, by conventional procedures for later reaction, $\underline{11}'a \rightarrow \underline{12}'$. The intermediate $\underline{12}'$ is prepared from $\underline{11}'a$ by treating $\underline{11}'a$ in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)-phosphine or the like. Typically, the reaction is conducted under a nitrogen atmosphere at a temperature of from −20° to 25° C., for from 0.5 to 2 hrs. The closure reaction $\underline{12} \rightarrow \underline{5}$ is accomplished by heating the phosphoraneazetidinone $\underline{12}$ in a solvent such as benzene, toluene dioxane, xylene, DMF or the like at a temperature of from 20° to 100° C. for from 0.25 hrs. to 5 days. The resulting penem is deblocked to yield I according to the previously described procedure.

In the generic representation of the compounds of the present invention (I):

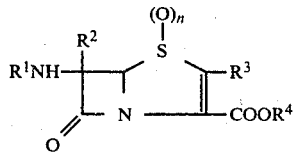

The preferred values for $R^3$ are: hydrogen; —R, —OR, —SR, —NR$_2$; wherein R is substituted or unsubstituted: alkyl having 1-6 carbon atoms, aryl such as phenyl, aralkyl wherein the aryl moiety is preferably phenyl and the alkyl has 1-6 carbon atoms such as benzyl, phenethyl and the like, heterocycyl or heterocyclyalkyl wherein the alkyl has 1-3 carbon atoms and the heterocyclic ring comprises 4-6 atoms, up to 4 of which may be selected from oxygen, sulfur and nitrogen; and wherein the chain or nuclear substituent on R is selected from: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxyl; the alkyl moieties of the above-recited substituents have 1-6 carbon atoms; n=0 is preferred.

The most preferred values for $R^2$ are hydrogen and methoxyl. The preferred ester moieties, $R^4$ (see $\underline{5}$, above) used as carboxyl protecting groups are those wherein $R^4$ is benzyl, p-nitrobenzyl, o-nitrobenzyl, t-butyl, bromo-t-butyl, t-butyl-dimethylsilyl, trimethylsilyl, trichloroethyl; $R^4$ may also represent in addition to hydrogen, pharmaceutically acceptable ester moieties such as pivaloyloxy-methyl, allyl, methallyl, (2-methylthio)-ethyl, or 3-buten-1-yl; and pharmaceutically acceptable salt cations.

Especially preferred embodiments of the present invention are those, as defined above, except that any unsubstituted amino group borne on radical $R^3$ of Structure I is derivatized according to the teachings of Belgium Pat. No. 848,545 (issued May 20, 1977); the resulting amino group being represented thusly (partial structure:

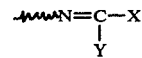

wherein X and Y are defined by the publication; species wherein X is H or lower alkyl and Y is NH$_2$ are especially preferred.

In the generic representation of the compounds of the present invention (I, above), the acyl radical represented by $R^1$ can be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acryl radicals can be represented by the general formula:

wherein X is O or S and R'' represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R'' is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl) vinyl, phenyl, o-methoxyphenyl, o-chlorophenyl, o-phenylphenyl, p-aminomethylbenzyl, 1-(5-cyanotrizolyl) methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)-methyl, 2- or 3-(5-methylthienyl)methyl, 2- or 3-(methoxythienyl)methyl, 2- or 3-(4-chlorothienyl)-methyl, 2- or 3-(5-sulfothienyl)methyl, 2- or 3-(5-carboxythienyl) methyl, 3-(1,2,5-thiadiazolyl)methyl, 3-(4-methoxy-1,2,5-thiadiazolyl)methyl, 2-furylmethyl, 2-(5-nitrofuryl) methyl, 3-furylmethyl, 2-theinylmethyl, 3-thienylmethyl, tetrazolylmethyl, benzamidinomethyl and cyclohexylamidinomethyl.

The acyl group can also be a radical of the formula:

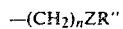

wherein X is O or S and n is 0–4, Z represents oxygen, sulfur, carbonyl or nitrogen and R'' is defined as above. Representative members of the substituent —(CH$_2$)$_n$ZR'' that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethl, p-(carboxymethyl)phenoxymethyl, p-(carboxymethyl)-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

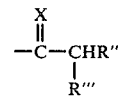

wherein R'' is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like.

Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(-)-α-hydroxybenzyl, α-carboxybenzyl, α-amino-(3-thienyl)methyl D(-)-α-amino-3-chloro-4-hydroxybenzyl, α-amino(cyclohexyl)methyl, α-(5-tetrazolyl)-benzyl, 2-thienyl-carboxymethyl, 3-thienylcarboxymethyl, 2-furyl-carboxymethyl, 3-furyl-carboxymethyl, α-sulfaminobenzyl, 3-thienyl-sulfaminomethyl, α-(N-methylsulfamino)-benzyl, D(-)-2-thienyl-guanidinomethyl, D(-)-α-guanidinobenzyl, α-guanylureidobenzyl, α-hydroxybenzyl, α-aziobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl containing one or more oxygen, sulfur or nitrogen atoms in the ring, such as furyl, quioxalyl, thienyl, quinolyl, quinazolyl, thiazolyl, isothiazolyl, tetrazolyl, oxadiazolyl, thiadiazolyl, and the like substituted heterocycles, phenylthio, phenyloxy, lower alkyl of 1-6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, amnioethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothaizolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolyl-acetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, poly- amino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate; trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 6-substituted amino-2-substituted-pen-2-em-3-carboxylic acids of the present invention are valuable antimicrobial substances which are active against various gram-positive and gram-negative pathogens. Thus, the free acid and especially the salts thereof such as amino and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solution or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl aclohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferably to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All temperatures are given in °C.

EXAMPLE 1

Preparation of 4-acetoxy-1-(1-benxyloxycarbonyl-2-methylprop-1-enyl)-3-methoxy-3-phenylacetamidoazetidin-2-one (7)

A stirred mixture of 454 mg (1 mmol) of benzyl-6-methoxy-6-phenylacetamido-penicillinate [L. D. Cama, W. J. Leanza and T. R. Beattie, and B. G. Christensen, JACS, 95, 1408 (1972)] and 637.4 mg (2.0 mmol) of mercuric acetate in 15 ml of glacial acetic acid is heated at 95° C. for 30 minutes. The cooled mixture is filtered and the filtrate is diluted with water. The mixture is neutralized with solid sodium bicarbonate and thoroughly extracted with chloroform. The combined chloroform extracts are washed successively with dilute aqueous sodium bicarbonate and brine. The chloroform solution is then dried (MgSO$_4$), filtered, and evaporated. Purification by plate layer chromatography provides 4-acetoxy-1-(1-benzyloxycarbonyl-2-methylprop-1-enyl)-3-methoxy-3-phenylacetamidoazetidin-2-one (7).

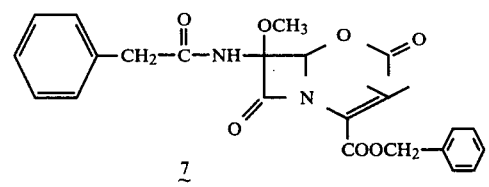

EXAMPLE 2

Preparation of 4-acetoxy-3-methoxy-2-phenylacetamidoazetidin-2-one (1)

To a stirred solution of 240 mg (0.5 mmol) of azetidinone prepared in Example 1 in 8 ml of 8:1 acetone-water and 2 drops of pH 7 0.1 N phosphate buffer at 25° C. is added 79 mg (0.5 mmol) of solid KMnO$_4$. The mixture is stirred under N$_2$ at 25° for 8 minutes and an additional 79 mg (0.5 mmol) of KMnO$_4$ is then added. The mixture is stirred further for 45 minutes and diluted with EtOAc. The mixture is treated with sufficient aqueous sodium thiosulfate to destroy any remaining permanganate. The mixture is then filtered through celite and washed thoroughly with ethyl acetate. The filtrate is partitioned between EtOAc/brine and the organic phase is separated, dried (MgSO$_4$), filtered and evaporated. Purification of the residue by plate layer chromatography affords 4-acetoxy-3-methoxy-3-phenylacetamido-azetidin-2-one (1).

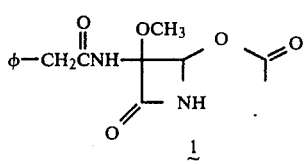

EXAMPLE 3

Preparation of 4-acetoxy-3-phenylacetamidoazetidin-2-one (1)

To a stirred solution of 4-acetoxy-1-(1-methoxycarbonyl-2-methylprop-1-enyl)-3-phenylacetamidoazetidin-2-one (709 mg, 1.9 mmol [R. J. Stoodley and N. R. Whitehouse, J. Chem. Soc., Perkin I, 32 (1973).] in 5 ml dimethylformamide, 5 ml pyridine and 1 ml water at 0° C. in an ice-water bath is added 497 mg (3.15 mmol) solid potassium permanganate. The mixture is stirred at 0° C. under a nitrogen atmosphere for 1.0 hour. The mixture is treated with sufficient aqueous sodium thiosulfate to destroy the excess permanganate and is diluted with ethylacetate. The mixture is filtered and the filtrate is partitioned between ethylacetate and dilute aqueous hydrochloric acid. The organic phase is separated and is washed successively with dilute aqueous sodium bicarbonate and brine. The organic phase is dried (MgSO$_4$), filtered, and evaporated. The residue is purified by plate layer chromatography [1 development φH-EtOAc (1:1)] to give 95.1 mg (19%) of 1; nmr (CDCl$_3$) 2.03, 3H(s); 3.5, 2H(s); 4.67; 1H(dd, J=1 Hz,7 Hz); 5.73, 1H(d, J=1 Hz); 7.17, 6H(s); 7.53, 1H(bs).

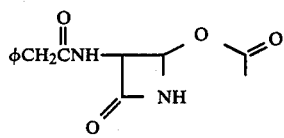

EXAMPLE 4

Following the procedures in the text and in Examples 1, 2, 3, the following 4-acetoxyazetidinones are obtained by analogy:

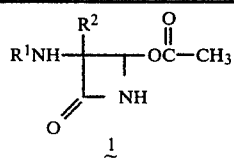

| Compound | R$^1$ | R$^2$ | Remarks |
|---|---|---|---|
| a | NHCH$_3$-C$_6$H$_4$-CH$_2$C(O)— | H | |
| b | NHCH$_3$-C$_6$H$_4$-CH$_2$C(O)— | OCH$_3$ | |
| c | φOCH$_2$C(O)— | H | lit. E. G. Brain, et al, J. CS, PI, 447 (1976); φ = phenyl. |

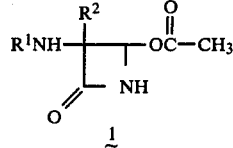

| Compound | R$^1$ | R$^2$ | Remarks |
|---|---|---|---|
| d | φOCH$_2$C(O)— | OCH$_3$ | |
| e | (thienyl)CH$_2$C(O)— | H | |
| f | (thienyl)CH$_2$C(O)— | OCH$_3$ | |
| g | NCCH$_2$C(O)— | H | |
| h | CF$_3$SCH$_2$C(O)— | H | |
| i | φ-CH(HNCO$_2$PNB)-C(O)— | H | |
| j | CF$_3$SCH$_2$C(O)— | OCH$_3$ | |
| k | NCCH$_2$C(O)— | OCH$_3$ | |
| l | CCl$_3$CH$_2$O$_2$CN(H)—(thiazine) | H | |

EXAMPLE 5

Preparation of 6-Phenylacetamido-2-aminoethylthio-pen-2-em-3-carboxylic acid I

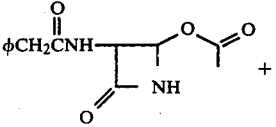

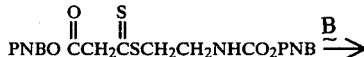
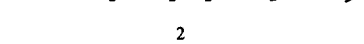

φ= phenyl        PNB = p-nitrobenzyl

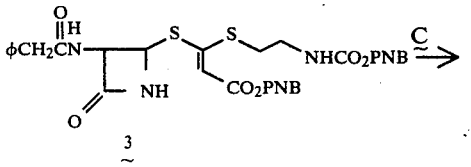

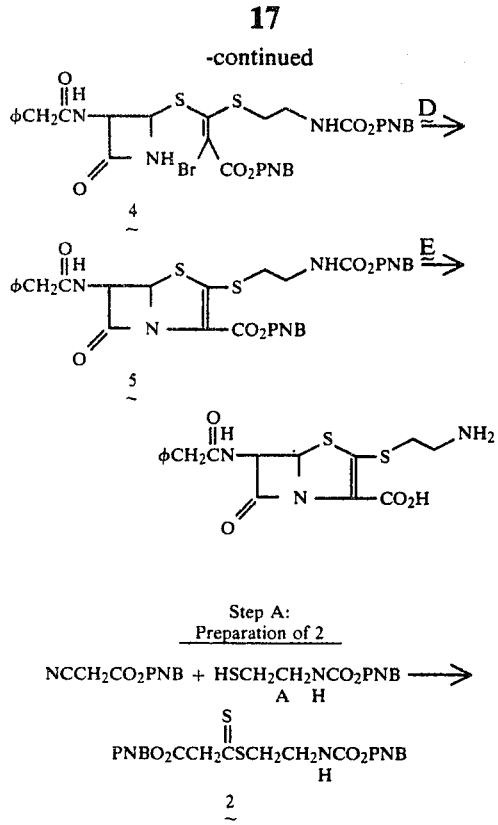

Step A:
Preparation of 2

NCCH₂CO₂PNB + HSCH₂CH₂NCO₂PNB ⟶
    A          H

PNBO₂CCH₂ĊSCH₂CH₂NCO₂PNB
                    H
         2

To a stirred solution of 3.77 g (17.2 mmol) of p-nitrobenzylcyanoacetate and 4.0 g (15,6 mmol) of N-p-nitrocbzcysteamine (A) in 40 ml dry benzene at 25° C. under a nitrogen atmosphere is introduce a stream of HCl(g) for 7 min. The reaction mixture is cooled on an ice-water bath and the introduction of HCl(g) continued for 3 min. The ice-water bath is removed and the mixture is stirred magnetically for 24 hrs. After this time, the solution is removed from the separated solid with the aid of a filter stick and the solid is washed with dry benzene (2×40 ml) in the same manner. The solid is dried in vacuo in the reaction flask, then dissolved in dry dimethylsulfoxide (DMSO) at 25° C. To the stirred solution is added an excess of H₂S(g) under nitrogen atmosphere for 10 min. and the mixture is stirred at 25° C. for 1.0 hr. The resulting orange colored solution containing some suspended material is poured into 200 ml cold H₂O and 200 ml Et₂O. The organic phase is separated and washed with H₂O (4×) and saturated NaCl(aq) solution, then dried over MgSO₄, filtered and evaporated to give 3.4 g of residue. Purification is accomplished by chromatography on silica gel eluting with benzene:ethylacetate (4:1) to give 2.1 g (67% based on 59% conversion) of 2 as a yellow-orange oil which slowly solidifies; IR(CHCl₃) 3400, 1720(sh), 1710, 1601, 1520 cm⁻¹; NMR (CDCl₃)δ: 3.45 (m, 4H); 4.08 (s, 2H); 5.1 (bs, 1H): 5.17 (s, 2H); 5.27 (s, 2H); 7.42 (d, J=8 Hz, 4H); 8.12 (d, J=8 Ha, 4H); mass spectrum m/e no 493(M+) 446, 256, 239, 209, 195, 165, 153, 136, 120.

Step B:

Preparation of Seco-Lactam 3

To a stirred mixture of 47.2 mg (0.18 mmol) of azetidinones 1 and 87.1 mg (0.18 mmol) of dithioate 2 in 1.5 ml of dry THF at 25° C. is added in one portion 50.5 mg (0.25 mmol) of solid aluminum isoproproxide [Al(O⁻<₃]. The mixture is stirred at 25° C. under N₂ for 6.0 hr. and is then partitioned between EtOAc and a cold, aqueous solution of dilute HCl-tartaric acid mixture. The EtOAc phase is separated and is washed with saturated NaCl(aq.), dried MgSO₄), filtered, and evaporated. Purification by plate layer chromatography yields 3.

Step C:

Preparation of Bromide 4

To a stirred solution of lactam 3 (59.1 mg, 0.085 mmol) and 15.1 mg (0.085 mmol HMPA (hexamethylphosphoramide in 2.0 ml dry THF (tetrahydrofuran) at 25° C. is added one portion 16.5 mg (0.093 mmol) solid NBS (N-brpomosuccinimide). The mixture is stirred at 25° C. under N₂ for 0.5 hr. and evaporated. The residue is partitioned between EtOAc and H₂O and the EtOAc phase is separated. It is further washed with H₂O (2x) and saturated NaCl (aq.), then dried (MgSO₄) filtered, and evaporated. Purification by repetitive plate layer chromatography yields 4.

Step D:

Preparation of penem 5

To a stirred mixture of 27.8 mg (0.04 mmol) of bromide 4 and 28 mg (0.14 mmol) of CuBr.S(CH₃)₂ in 5 ml dry THF at −78° C. under N₂ is added 2 ml of a cold, freshly prepared solution of lithium diisopropylamide, LiN( )₂, [generated at 0°/20 min. with 5 mg (0.05 mmol) HN( )₂ (diisopropylamine) and 19 μl of 2.4 M buLi (butyllithium)]. The mixture is stirred over the following temperature ranges for the times indicated: −78° to −74° (40 min.); −74° to −68° (30 min.); −68° to −57° (30 min.); −57° to −41° (20 min.); −41° to −26° (20 min.); −26° to −20° (28 min.); −20° to −13° (38 min.); −15° to −9° (53 min.); −10° to −5° (18 min.); and −5° to 0° (18 min.). The mixture is then treated at 0° with 1 ml of saturated NH₄Cl (aq.) and diluted with Et₂O/H₂O. The organic phase is separated and washed further with aqueous NH₄Cl and saturated NcCl (aq.). The organic layer is dried (MgSO₄), filtered, and evaporated. The residue is purified by plate layer chromatography to yield 5.

Step E:

Preparation of Penem I

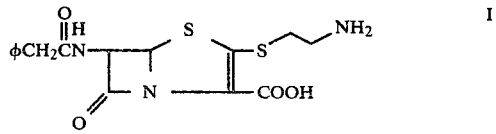

To 10 mg of 5 (Step D, above) is added 0.60 ml dioxane, 0.05 ml ethanol, 0.35 ml deionized water and 0.01 ml of 1.0 M K₂HPO₄. To the resultant clear solution is added 5 mg of 10% Pd/C. The suspension is flushed with N₂m then 5–6 times alternately with 50 psi H₂ and vacuum. Finally, it is shaken under a 50 psi H₂ atmosphere for 30–40 min. After centrifugation, the Pd/C is washed and centrifuged 2-3X with 0.5 ml portions of deionized water. The combined centrifugates are extracted 5×1−2 ml ether. Residual ether is removed under vacuum and the aqueous solution applied to an XAD-2 column (20×140 mm). Fractions of 100 drops (6–7 ml) are collected, with continuous UV monitoring, by elution with deionized water. The chosen fractions are combined and lyophilized to provide I.

EXAMPLE 6

Preparation of RSCCH$_2$CO$_2$R$^2$(2);
R = CH$_3$, R$^2$ = PNB (p-nitrobenzyl)

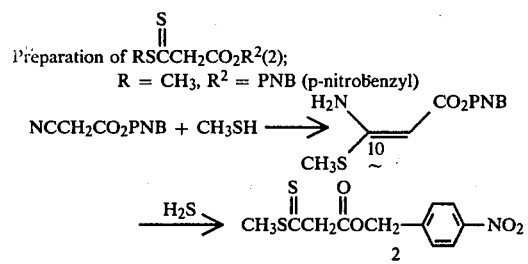

To a stirred mixture of 11.0 g (0.05 mol) of p-nitrobenzylcyanoacetate and 3.72 g (0.078 mol) methylmercaptan in 200 ml of sodium dried benzene at 25° C. is introduced a stream of HCl(g) until 1.85 g (0.05 mmol) is added. The mixture is then stirred at 25° C. under nitrogen atmosphere for 74.5 hrs. The solution is decanted away from the separated solid and the moist precipitate is dissolved in 50 ml of dry pyridine. (Alternatively the precipitate is dissolved in dry dimethylsulfoxide and treated with H$_2$S(g) as described below to afford 2 directly.) The pyridine solution is treated with excess H$_2$S(g) and is stirred at 25° C. under nitrogen atmosphere for 2 hrs. The reaction mixture is poured into ice/water and extracted with ether. The separated extract is washed twice with water and twice with brine solution then dried over MgSO$_4$, filtered, and evaporated to give a crystalline mass. Recrystallization from ether gives 5.0 g of the enamide 10; ir(CHCl$_3$), 3636, 3322, 1664, 1592, 1517 cm$^{-1}$; NMR (CDCl$_3$)δ: 2.4 (s, 3H), 4.68 (s, 1H); 5.17 (s, 2H); 6.43 (bs, 2H); 7.43 (d, J=8 Hz, 2H); 8.13 (d, J=8 Hz, 2H); mass spectrum m/e 268 (M+), 221, 175, 136. Purification of the mother liquors from above by column chromatography on silica gel eluting with CHCl$_3$-pet-ether (1:;) provides 940 mg of 2 as an orange oil: ir (CHCl$_3$) 1742, 1613, 1522; NMR (CDCl$_3$)δ2.67 (s, 3H); 4.13 (s, 2H); 5.23 (s, 2H); 7.47 (d, J=9 Hz, 2H); 8.17 (d, J=9 Hz, 2H); mass spectrum m/e 285 (M+), 238, 136, 106. The enamide 10 is converted to 2 by the following procedure.

The crude enamide 10 7.9 g (29 mmol) is dissolved in 40 ml of dry DMF (dimethylformamide) at 25° C. and is treated successively with 3.7 g (32 mmol) of trifluoroacetic acid and excess hydrogen sulfide. The resulting mixture is stirred magnetically at 25° C. under CaCl$_2$ drying tube protection for 5 hrs. The mixture is poured into 75 ml ice-H$_2$O and extracted with 100 ml Et$_2$O (diethylether). The separated etheral extract is washed twice with H$_2$O and saturated NaCl(aq) solution, then dried with MgSO$_4$, filtered, and evaporated. Purification by column chromatography on silica gel eluting with CHCl$_3$-petroleum ether (1:1) gives 6.55 g (74%) of 2.

EXAMPLE 7

Preparation of dithioate derivative 2,

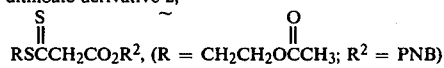

RSCCH$_2$CO$_2$R$^2$, (R = CH$_2$CH$_2$OCCH$_3$; R$^2$ = PNB)

To a stirred mixture of 6.78 g (5.6 mmol) of 2-acetoxyethyl mercaptan and 11.0 g (5 mmol) p-nitrobenzylcyanoacetate in 100 ml of dry benzene is introduced 3.0 g (8.1 mmol) of hydrogen chloride gas. The mixture is stirred under N$_2$ at RT (25° C.) for 42 hours after which time the solution is decanted away from the oily mass. The mass is washed twice with dry benzene by decantation. The oil is dissolved in 20 ml of dry dimethylformamide and is treated with a vigorous stream of hydrogen sulfide (g) for 5 min. The mixture is stirred at 25° C. for 5 hours and then is poured into ice cold water and is extracted with ether. The ether extract is washed well with water, then brine, and is dried over MgSO$_4$, filtered, and evaporated. Purification by column chromatography on silica gel provides the dithioate derivative 2 as an orange solid; ir (CHCl$_3$) 1770, 1600, 1538 cm$^{-1}$; nmr (CDCl$_3$)δ: 2.03, 3H(s); 3.53, 2H(t,J=6 Hz); 4.1, 2H(s); 4.27, 2H(t,J=6 Hz); 5.25, 2H(s); 7.46, 2H(d,J=9 Hz); 8.2, 2H(d,J=9 Hz); mass spectrum m/e 357(M+), 297, 271, 206, 169, 136.

EXAMPLE 8

Preparation of Benzyl-thiobenzoylacetate 2;

$$\overset{S}{\underset{\|}{R\text{C}}}\text{CH}_2\text{CO}_2\text{R}^2 \ (R = phenyl; R^2 = benzyl):$$

Into a stirred solution of 19.2 g of benzylacetoacetate in 150 ml of acetonitrile at −60° C. is passed a stream of hydrogen sulfide gas for 1.5 hours, followed by dry HCl(g) for 40 min. The reaction solution is then let warm to −20° C. and is poured into ice water. The product 2 is extracted into benzene and purified by vacuum distillation to provide the known benzyl-thiobenzoylacetate, bp 09° (0.05 mm).

EXAMPLE 9

Following the procedure described in the foregoing text and Examples, the following starting reagents 2 necessary for the preparation of the compounds of the present invention are representatively obtained by analogy.

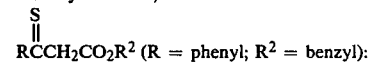

| Compound | R$^3$ | R$^4$ |
|---|---|---|
| (1.) | —S—[1-methyl-imidazol-2-yl] | —CH$_2$—C$_6$H$_4$—NO$_2$ |
| (2.) | —SCH$_3$ | " |
| (3.) | —S—phenyl | " |
| (4.) | —S—pyridyl | " |
| (5.) | —S—thienyl | " |
| (6.) | —S—furyl | " |
| (7.) | —SCH$_2$—C$_6$H$_4$—CH$_2$NCO$_2$PNB (H) | " |
| (8.) | —SCH$_2$NHCOCH$_2$—C$_6$H$_4$—NO$_2$ | " |
| (9.) | —SCH$_2$CH$_2$OCCH$_3$ (O) | " |

-continued

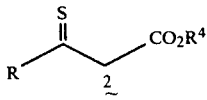

| Compound | $R^3$ | $R^4$ |
| --- | --- | --- |
| (10.) | —SCH$_2$CH$_2$OSi(CH$_3$)$_2$C(CH$_3$)$_3$ | " |
| (11.) | phenyl | benzyl |
| (12.) | methyl | -p-nitrobenzyl |
| (13.) | 2-furyl | " |
| (14.) | 2-thienyl | " |
| (15.) | 2-pyridyl | " |
| (16.) | 2-N-methyltetrazolyl | " |
| (17.) | benzyl | " |
| (18.) | 2-thiatriazolyl | " |
| (19.) | p-trifluoromethylthiophenyl | " |
| (20.) | p-nitrophenyl | " |
| (21.) | 2-thienylmethyl | " |
| (22.) | 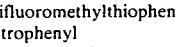 | " |

EXAMPLE 10

Preparation of Seco-lactam

To a stirred mixture of acetoxyazetidinone (Example 3) (95.1 mg., 0.36 mmol) and 139.2 mg (0.49 mmol) of the dithioate reagent 2 of Example 6 (compound 2) in 5 ml methanol at 25° C. is added 22 mg (0.4 mmol) sodium methoxide. The mixture is stirred under N$_2$ for 17 hours and an insoluble product is collected by filtration to provide 22 mg (12.5%) of a single trans olefin isomer 3: nmr (d$_6$-DMSO 2.43, 3H(s); 3.5, 2H(s); 4.7, 1H(m); 5.3, 2H(s); 5.36, 1H(d, J=2 Hz); 5.83, 1H(s); 7.3, 5H(s); 7.67, 2H(d,J=8 Hz); 8.27, 2H(d,J=8 Hz); 8.9, 1H(d,J=8 Hz); 9.03, 1H(bs); mass spectrum m/e 470(M$^+$ —17); 442, 352, 285, 202, 159, 136, 106, 91. The filtrate above is evaporated and the residue is partitioned between EtOAc/brine. The organic is separated, dried (MgSO$_4$), filtered and evaporated. Purification by plate layer chromatography [1 development φH-EtOAc(1:1)] provides two separable product fractions: 28.5 mg of more non-polar material as a mixture of isomers: nmr (CDCl$_3$) 2.37 and 2.43, 3H(s); 3.57, 2H(s); 4.77, 1H(m): 5.2, 2H(s); 5.3, 1H(m); 5.63 and 5.83, 1H(s); 6.6, 1H(m); 6.87, 1H(m); 7.23, 5H(s); 7.5, 2H(d,J=8 Hz); 8.2, 2H(d,J=8 Hz); mass spectrum m/e 470 (M$^+$ —17), 442, 352, 285, 202, 159, 136, 91; and 37.4 mg of more polar material as a mixture of isomers: nmr (CDCl$_3$) 2.27, 3H(s); 3.53, 2H(s); 5.23, 2H(s); 5.6, 3H(m); 7.07, 2H(m); 7.23, 5H(s); 7.5, 2H(d,J=8 Hz); 8.2, 2H(d,J=8 Hz). Total yield of isomers 3 is 88 mg (50%).

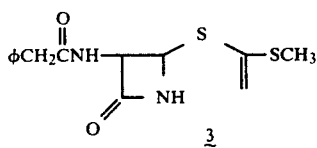

EXAMPLE 11

Preparation of Bromide 4

To a stirred solution of 50.5 mg (0.104 mmole) of non-polar lactams 3 of Example 10 and 18 mg (0.1 mmole of hexamethylphosphoramide in 2 ml of dry tetrahydrofuran at 25° C. is added 17.8 mg (0.1 mmole) of N-bromosuccinimide. The mixture is stirred at 25° C. under N$_2$ for 0.5 hours, after which time the solvent is evaporated. The residue is purified by plate layer chromatography to yield the desired bromide 4.

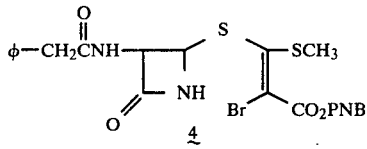

EXAMPLE 12

Preparation of p-Nitrobenzyl-6-phenylacetamido-2-thiomethyl-pen-2-em-3-carboxylate (5)

To a stirred solution of bromide derivative 4a (56.6 mg, 0.1 mmol) and cuprous bromide-dimethylsulfide complex (67.7 mg, 0.33 mmol) in 10 ml of dry tetrahydrofuran at —78° C. under N$_2$ is added a cold, freshly prepared solution of lithium diisopropylamide (0.11 mmol) in 4 ml dry tetrahydrofuran. The mixture is stirred from —78° C. to 0° C. over a 6 hour period. At 0° C. the mixture is treated with 2 ml of saturated, aqueous ammonium chloride solution. The mixture is then partitioned between ether and water and the organic phase is separated. The organic extract is washed successively with saturated, aqueous ammonium chloride solution. The mixture is then partitioned between ether and water and the organic phase is separated. The organic extract is washed successively with saturated, aqueous ammonium chloride and brine followed by drying (MgSO$_4$), filtering, and evaporating. The residue so obtained is purified by plate layer chromatography to provide penem derivative 5.

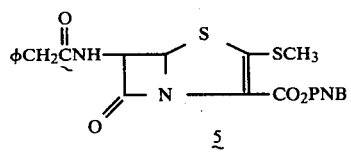

EXAMPLE 13

Preparation of Sodio-6-phenylacetamido-2-thio-methyl-pen-2-em-3-carboxylate (I)

A mixture of 20 mg of 10% Pd/C, 10 mg (0.2 mmol) of p-nitro-benzyl-6-phenylacetamido-2-thiomethyl pen-2-em-3-carboxylate (5 of Example 12) and 1.7 mg of sodium bicarbonate in 1 ml of ethylacetate, 0.2 ml isopropanol, and 1 ml of 0.5 N pH 7 phosphate buffer is hydrogenated at RT and 40 psi in a Parr shaker for 15 minutes. The catalyst is removed by filtration and is washed thoroughly with deionized water. The filtrate is collected in a cold receiver. The cold filtrate is thoroughly extracted with ethyl acetate and the phases are separated. The aqueous phase is acidified to pH~2.5 with cold 1 M ph~2.0 phosphate buffer and is then extracted with cold ethyl acetate. The separated ethyl acetate extract is then shaken with an aqueous solution of sodium bicarbonate (7 mg, 0.02 mmol). The aqueous phase is separated and lyophylized to provide sodio-6-phenyl-acetamido-2-thio-methylpen-2-em-3-carboxylate (I).

In cases where the above procedure produces zwitterionic species, the procedure is modified as follows: After the filtrate is extracted thoroughly with EtOAc, the cold aqueous phase is brought to a pH 7 and chromatographed on XAD-2 resin to afford the desired penem zwitterionic species.

EXAMPLE 14

Preparation of Sodio-6-phenylacetamido-6-Methoxy-2-phenyl-pen-2-em-3-carboxylate

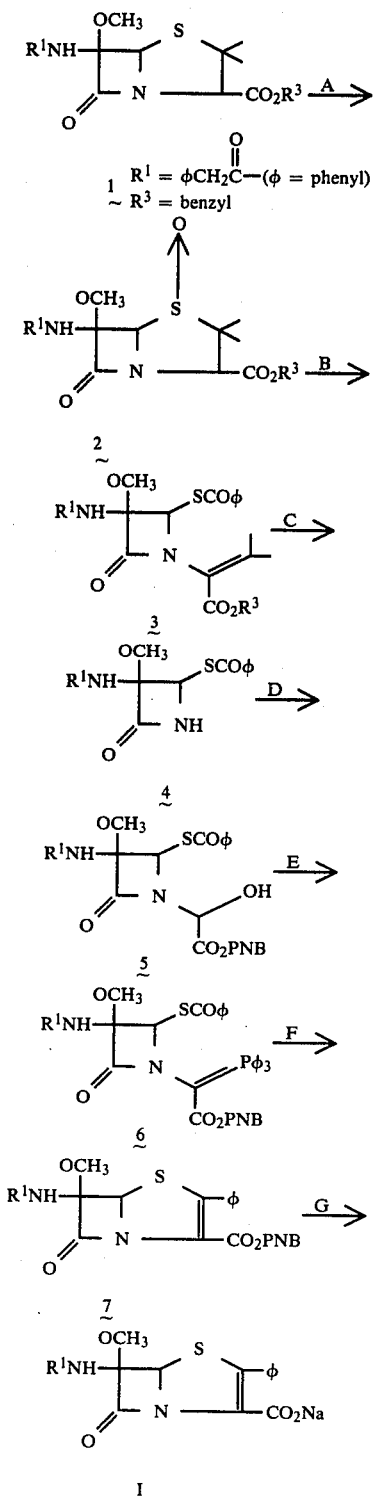

Step A

To a stirred solution of 567.5 mg (1.25 mmoles) of benzyl-6-methoxy-6-phenyl acetamidopenicillanate in 15 ml. methylene chloride at 25° C. is added all at once 253.8 mg (1.25 mmoles) of 85% m-chloroperbenzoic acid. The mixture is stirred under an atmosphere of nitrogen at 25° C. for 15 min. and is then partitioned between ethyl acetate and ice cold, aqueous sodium bicarbonate solution. The organic phase is separated, washed further with saturated, aqueous sodium chloride solution, dried (MgSO$_4$), filtered, and evaporated. The residue is purified by plate layer chromatography (PLC) to provide the desired sulfoxide.

Step B

A stirred mixture of 94 mg (0.2 mmoles) of the sulfoxide obtained in Step A, 49 mg (0.24 mmoles) of tri-n-butylphosphine, and 229 mg (1.0 mmoles) of benzoic anhydride in 3.0 ml of benzene is refluxed at 90° C. under a nitrogen atmosphere for 7.0 hours. The cooled mixture is partitioned between ethyl acetate and cold, aqueous sodium bicarbonate and the organic phase is separated. The organic phase is washed with saturated, aqueous sodium chloride, dried (MgSO$_4$), filtered, and evaporated. Purification by PLC provides 3.

Step C

To a stirred solution of 20.7 mg (0.036 mmoles) of azetidinone 3 in 0.75 ml. of 8:1 acetone-water and two drops of 0.1 N pH 7 phosphate buffer at 25° C. is added all at once 5.7 mg (0.036 mmoles) of potassium permanganate. The mixture is stirred at 25° C. under nitrogen for 8 min and then an additional 5.7 mg of potassium permanganate is added. The mixture is stirred further for 50 min. and is then cooled on an ice-water bath, diluted with ethyl acetate, and is treated with 5% aqueous sodium thiosulfate. The mixture is filtered through celite and is washed well with ethyl acetate. The filtrate is partitioned between ethyl acetate and cold, aqueous brine solution and the organic phase is separated, dried (MgSO$_4$), filtered, and evaporated. The residue is purified by PLC to give 4.

Step D

A stirred mixture of 10.4 mg (0.027 mmoles) of azetidinone 4 (Step C) and a large excess of p-nitrobenzylglyoxalate hydrate in 1 ml of toluene and 0.5 ml of dimethyl formamide containing 500 mg of ground 3 A molecular sieves is heated at 80° C. under a nitrogen atmosphere for 5.0 hr. The cooled mixture is diluted with ethyl acetate and is filtered. The filtrate is concentrated on a rotary evaporator and the concentrate is partitioned between diethyl ether and cold water. The organic phase is separated, washed further with water, dried (MgSO$_4$), filtered, and evaporated. The residue is purified by PLC to give 5.

Step E

To a stirred solution of 11.9 mg (0.02 mmoles) of lactam 5 from Step D in 1.0 ml anhydrous tetrahydrofuran at 0° C. under a nitrogen atmosphere is added in rapid succession 2.4 mg (0.02 mmoles) of neat thionyl chloride and 2.0 mg (0.02 mmoles) of neat triethyl amine. The mixture is stirred at 0° C. for 2.0 hours and is then partitioned between diethyl ether and cold, aqueous brine. The organic phase is separated, washed with saturated, aqueous sodium chloride, dried (MgSO4), filtered, and evaporated. The residue so obtained is dissolved in 0.5 ml dry tetrahydrofuran and stirred with 10.0 mg (0.04 mmoles) of triphenylphosphine at 50° C. under a nitrogen atmosphere for 18.0 hrs. The cooled mixture is partitioned between ethyl acetate and aqueous sodium bicarbonate solution. The organic phase is separated, dried (Na2SO4), filtered and evaporated. Purification of the residue by PLC affords the phosphorane derivative 6.

Step F

A stirred solution of 83.9 mg (0.1 mmole) of phosphoraneazetidinone (Step E) in 80 ml of toluene is heated at 85° C. under an atmosphere of nitrogen for 3.5 days. The toluene is removed under reduced pressure and the residue is purified by plate layer chromatography to provide penem 7.

Step G

A mixture of 56.1 mg (0.1 mmoles) of penem 7, 150 mg of 10% palladium-on-charcoal, and dilute, aqueous sodium bicarbonate in 5 ml. of ethyl acetate is hydrogenated at 25° C. and atmospheric pressure for 30 minutes. After this time 25 mg of fresh catalyst is added and the mixture is hydrogenated for an additional 5 minutes. The catalyst is removed by filtration and washed with dilute, cold aqueous sodium bicarbonate and ethyl acetate. The organic phase is separated and the aqueous phase acidified with dilute, cold aqueous citric acid. Thorough extraction of the acidified aqueous phase with methylene chloride, followed by drying (Na2SO4) and evaporation, provides the penem carboxylic acid 8, which is immediately converted to its dodium salt by treatment with a stoichiometric amount of aqueous sodium bicarbonate in acetone solution, evaporation of acetone, and lyopholization of the aqueous solution.

EXAMPLE 14A

Preparation of:

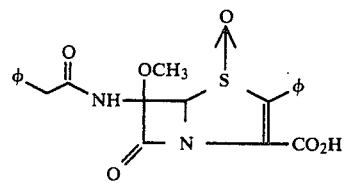

To a stirred solution of 0.1 mmoles of penem 7 from Example 14, Step F, in 2 ml of methylene chloride at 25° C. is added 20.3 mg (0.1 mmoles) of 85% m-chloroperbenzoic acid. The mixture is stirred at 25° C. under a nitrogen atmosphere for 0.5 hours and then is partitioned between methylene chloride and and cold, dilute aqueous sodium bicarbonate. The organic phase is separated, dried (Na2SO4), filtered and evaporated to yield the desired sulfoxide.

The above illustrated carboxylic acid is obtained as described in Step G of Example 14 when the indicated substitution is made by the catalytic hydrogenation of the sulfoxide prepared above.

EXAMPLE 15

Following the procedure of the foregoing Examples and text, the following species of the invention are obtained by analogy:

| Compound | $R^1$ | $R^2$ | $R^3$ | $R^4$ |
|---|---|---|---|---|
| 1. | φCH2C(O) | H | SCH3 | Na |
| 2. | φCH2C(O) | H | SCH2CH2NH2 | H |
| 3. | φCH2C(O) | OCH3 | SCH2CH2NH2 | H |
| 4. | φCH2C(O) | H | S-(N=N-N(CH3)-N=) triazole | Na |
| 15. | φOCH2C(O) | H | S-pyridyl | Na |
| 16. | φOCH2C(O) | OCH3 | SCH3NH2 | H |
| 17. | thienyl-CH2C(O) | H | SCH2CH2NH2 | H |
| 18. | thienyl-CH2C(O) | OCH3 | SCH2CH2NH2 | H |
| 19. | NCCH2C(O) | OCH3 | SCH2CH2NH2 | H |

-continued $$R^1NH \underset{O}{\overset{R^2}{-}} \overset{S}{\underset{N}{\bigsqcup}} \overset{R^3}{\underset{COOR^4}{}}$$

I

| Compound | $R^1$ | $R^2$ | $R^3$ | $R^4$ |
|---|---|---|---|---|
| 20. | CF$_3$SCH$_2$C(O)– | OCH$_3$ | SCH$_2$CH$_2$NH$_2$ | H |
| 21. | φ–CH(NH$_2$)–C(O)– | H | S-(N—N=N-N(CH$_3$)) tetrazolyl | H |
| 22. | φCH$_2$C(O)– | H | φ | Na |
| 23. | φOCH$_2$C(O)– | H | N-(N—N=N-N(CH$_3$)) tetrazolyl | Na |
| 24. | CF$_3$SCH$_2$C(O)– | OCH$_3$ | S-(N—N=N-N) thiadiazolyl | Na |
| 25. | (2-thienyl)-CH$_2$C(O)– | OCH$_3$ | –C$_6$H$_4$–OCH$_3$ | Na |
| 26. | φ–CH(NH$_2$)–C(O)– | H | 2-thienyl | H |
| 27. | H$_2$N–(thiazolyl)–CH$_2$C(O)– | H | –C$_6$H$_4$–CH$_2$NH$_2$ | H |

EXAMPLE 16

Preparation of Pharmaceutical Compositions

One such unit dosage form is prepared by mixing 120 mg. of 6-phenylacetamido-2-aminoethylthio-pen-2-em-3-carboxylic acid with 2- mg. of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-phenylacetamido-2-aminoethylthio-pen-2-em-3-carboxylic acid | 125 mg. |
| Dicalcium Phosphate | 192 mg. |
| Cornstarch, U.S.P. | 6 mg. |
| Lactose, U.S.P. | 190 mg. |
| Magnesium Stearate | balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 6-phenylacetamido-2-aminoethylthio-pen-2-em-3-carboxylic acid | 500 mg. |
| Diluent: Sterile Water for Injection | 2 cc |
| OPTHALMIC SOLUTION | |
| 6-phenylacetamido-2-aminoethylthio-pen-2-em-3-carboxylic acid | 100 mg. |
| Hydroxypropylmethyl cellulose | 5 mg. |
| Sterile Water | to 1 ml. |
| OTIC SOLUTION | |
| 6-phenylacetamido-2-aminoethylthio-pen-2-em-3-carboxylic acid | 100 mg. |
| Benzalkonium chloride | 0.1 mg. |
| Sterile Water | to 1 ml. |
| TOPICAL OINTMENT | |
| 6-phenylacetamido-2-aminoethylthio-pen-2-em-3-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A process for preparing a compound of the structure:

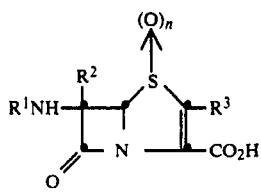

and the pharmaceutically acceptable salts and esters thereof wherein $R^2$ is hydrogen or methoxyl and $R^1$ is hydrogen or acyl and $R^3$ is hydrogen, —R, —OR, —SR, —NR$_2$; wherein R is substituted or unsubstituted: alkyl having 1-6 carbon atoms, phenyl, phenylalkyl having 7-12 carbon atoms, heterocyclyl and heterocyclylalkyl wherein the alkyl has 1-3 carbon atoms and the heterocycle has 1-4 hetero atoms selected from O, N and S; and wherein the chain or nuclear substituent on R is selected from amino, mono-, di- and trialkylamino (each alkyl having 1-6 carbon atoms), hydroxyl, alkoxyl, having 1-6 carbon atoms, mercapto, alkylthio having 1-3 carbon atoms, phenylthio, sulfamoyl, amidino, guanidino, nitro, chloro, bromo, fluoro, cyano and carboxyl; n is 0 or 1; when n=1, $R^3$ is not —SR; comprising cyclizing:

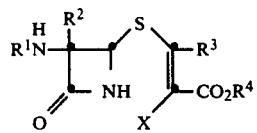

in the presence of a strong base in the presence of a metal complex coupling agent; wherein $R^4$ is a protecting group or a pharmaceutically acceptable ester moiety and X is halo.

2. A process for preparing a compound of the structure:

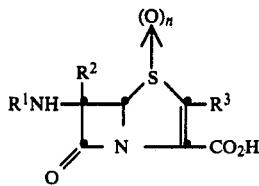

and the pharmaceutically acceptable salts and esters thereof wherein $R^2$ is hydrogen or methoxyl and $R^1$ is hydrogen or acyl and $R^3$ is hydrogen, —R, —OR, —SR, —NR$_2$; wherein R is substituted or unsubstituted: alkyl having 1-6 carbon atoms, phenyl, phenylalkyl having 7-12 carbon atoms, heterocyclyl and heterocyclylalkyl wherein the alkyl has 1-3 carbon atoms and the heterocycle has 1-4 hetero atoms selected from O, N and S; and wherein the chain or nuclear substituent on R is selected from amino, mono-, di- and trialkylamino (each alkyl having 1-6 carbon atoms), hydroxyl, alkoxyl, having 1-6 carbon atoms, mercapto, alkylthio having 1-3 carbon atoms, phenylthio, sulfamoyl, amidino, guanidino, nitro, chloro, bromo, fluoro, cyano and carboxyl; when $R^2$ is hydrogen, $R^3$ is not hydrogen or R; n is 0 or 1; when n=1, $R^3$ is not —SR; comprising heating:

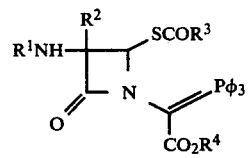

wherein $\phi$ is phenyl and $R^4$ is a protecting group or a pharmaceutically acceptable ester moiety.

* * * * *